United States Patent [19]

Hara et al.

[11] Patent Number: 4,953,405
[45] Date of Patent: Sep. 4, 1990

[54] ULTRASONIC MEASURING APPARATUS FOR MEASURING A PREDETERMINED BOUNDARY SURFACE INSIDE AN OBJECT

[75] Inventors: Kazuhiko Hara, Yokohama; Toshiaki Takahashi, Tachikawa; Masato Nagura, Chofu, all of Japan

[73] Assignee: Canon Kabushiki Kaisha, Tokyo, Japan

[21] Appl. No.: 329,814

[22] Filed: Mar. 28, 1989

[30] Foreign Application Priority Data

Mar. 29, 1988 [JP]  Japan ................................. 63-77829

[51] Int. Cl.$^5$ ............................................. G01N 29/00
[52] U.S. Cl. .................................... 73/602; 73/620
[58] Field of Search ............... 73/588, 620, 589, 598, 73/602, 606, 627

[56] References Cited

U.S. PATENT DOCUMENTS

| | | | |
|---|---|---|---|
| 3,934,458 | 1/1976 | Beretsky et al. | 73/602 |
| 4,100,808 | 7/1978 | Evans et al. | 73/588 |
| 4,193,306 | 3/1980 | Flaherty et al. | 73/629 |

OTHER PUBLICATIONS

"H-F Ultrasonic Testing of Bonds: Application to Silicon Power Devices" by R. S. Gilmore et al., Materials Evaluation/Jan. 1979.

Primary Examiner—Hezron E. Williams
Assistant Examiner—Louis M. Arana
Attorney, Agent, or Firm—Fitzpatrick, Cella, Harper & Scinto

[57] ABSTRACT

An ultrasonic measuring method and an ultrasonic measuring apparatus utilize the level of a reflected ultrasonic reception signal coming from an object to be examined as measurement data after the level has been provided with either a positive or a negative sign in accordance with the phase of the reception signal.

7 Claims, 4 Drawing Sheets

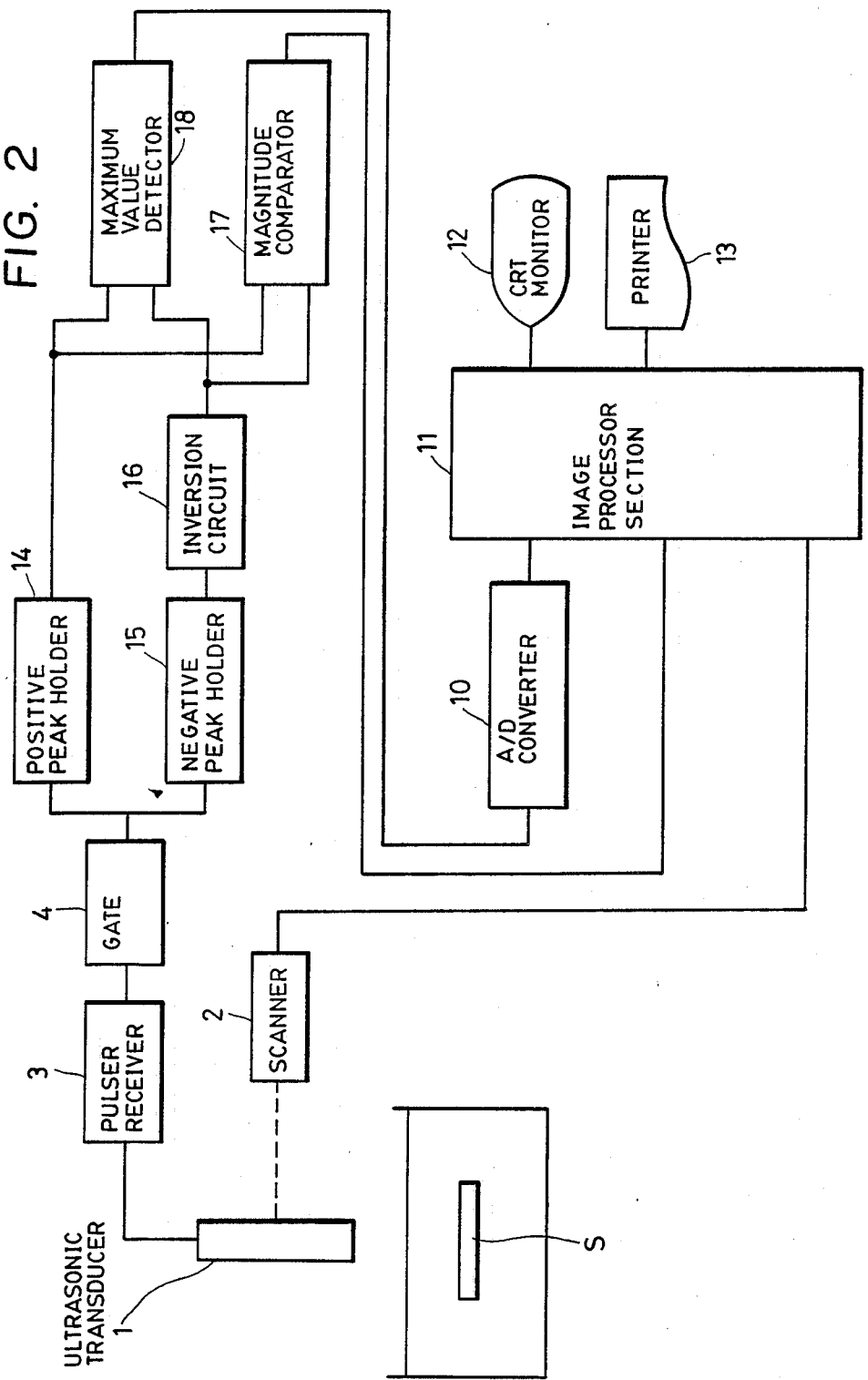

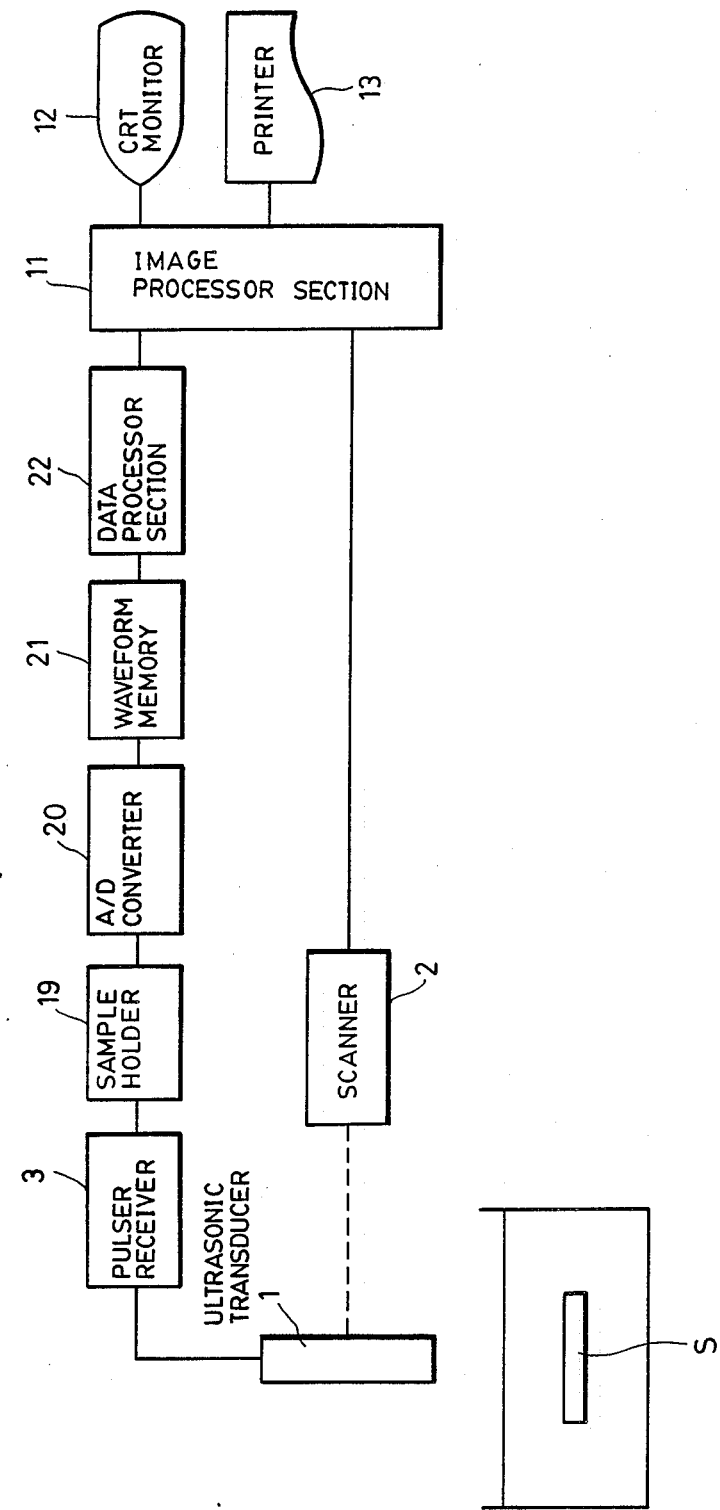

TH1 ———— POSITIVE COMPARATOR
TH2 ———— NEGATIVE COMPARATOR

ULTRASONIC MEASURING APPARATUS FOR MEASURING A PREDETERMINED BOUNDARY SURFACE INSIDE AN OBJECT

BACKGROUND OF THE INVENTION

1. Field of the Invention

This invention relates to an ultrasonic measuring method and an ultrasonic measuring apparatus for examining the inside of an object by the ultrasonic pulse echo method.

2. Description of the Related Art

The ultrasonic pulse echo method is well known as a method of detecting any cracks or peelings inside an object without breaking it.

The principle of the ultrasonic pulse echo method will be illustrated below along with the process for obtaining an ultrasonic image through this method.

A sound wave is partly reflected by an acoustically discontinuous surface (boundary surface). The reflectance R can be expressed as:

$$R = |(Z_2 - Z_1)/(Z_2 + Z_1)| \tag{1}$$

wherein $Z_1$ expresses the material impedance on the incidence side, and $Z_2$ that on the transmission side. Further, it is known that in the case of a reflection on a boundary surface where $Z_2 < Z_1$, a phase inversion occurs between the incidence and the reflected waves. In the ultrasonic pulse echo method, an ultrasonic pulse is transmitted to the object to be examined to generate a reflection signal. By passing the reflection signal through a time gate of a suitable time constant, the reflection signal which comes from the inside of the object can be extracted. The inner condition of the object can be examined by measuring the level of the reflection signal thus extracted.

Considered here will be how any peeling between plastic and metal surfaces can be detected by this method.

A transmission pulse sent from an ultrasonic transducer is partly transmitted through the plastic surface to become an incidence wave on the boundary surface between the plastic and metal surfaces, the phase of the transmission pulse being maintained. The reflectance on the boundary surface between the plastic and metal surfaces is ca. 50% as given by the above equation (1), no phase inversion occurring since $Z_1 < Z_2$. When an air layer is generated as a result of peeling, the ultrasonic pulse is reflected by the boundary surface between the air and the plastic surface. Since the reflectance is about 100%, and $Z_1 > Z_2$, a phase inversion occurs. In an actual measurement, it is difficult to measure the absolute reflectance because of the damping of the sound wave due to absorption, dispersion and the like. Accordingly, peelings are detected by comparing the level of the reflection signal from them with that of the signal from the close-contact area.

However, if the covering of the entire measurement area has been peeled off, it is difficult, in the above-described conventional method, to judge whether the area is in the peeled or the close-contact condition. In the case of a fine peeling in which peelings partially exist within the diameter of the ultrasonic beam, the signal with no phase inversion from the close-contact area and that with inverted phase from the peeling area may combine with each other to form a synthetic wave, canceling each other to lower the signal level. As a result, the signal level of the synthetic wave is lower than that of the wave from the close-contact area, thereby leading to confusion in discriminating between close-contact and peeling areas.

The above problem is eliminated in a conventional measuring method by using a single-shot pulse with an asymmetrical waveform as the transmission pulse. According to this conventional method, the positive and the negative peaks of the reception signal are caught so as to obtain the difference in absolute value between them as the reflection signal level, which includes the phase inversion. The problem with an apparatus using this method is that the difference between the peak values is rather small when the waveform of the transmission signal is not sufficiently asymmetrical, so that it is difficult to detect. Furthermore, when the asymmetry is lessened by any irregularity in the waveform due to the condition of the boundary surface, the difference between the positive and negative peak values becomes smaller in spite of the high magnitude of the signal itself, so that the signal level, which is represented by the difference, is lowered, which inevitably makes it difficult to discriminate between the close-contact and the peeling areas.

SUMMARY OF THE INVENTION

Accordingly, it is an object of this invention to provide an ultrasonic measuring method and an ultrasonic measuring apparatus capable of correctly discriminating between peeling and close-contact areas in an object to be examined by detecting the phase of an ultrasonic reflection signal.

BRIEF DESCRIPTION OF THE DRAWINGS

FIG. 2 is a block diagram showing a second embodiment of the apparatus;

FIG. 3 is a block diagram showing a third embodiment of the apparatus;

DESCRIPTION OF THE PREFERRED EMBODIMENTS

Embodiments of this invention will now be described in detail with reference to the attached drawings.

Figure 1:
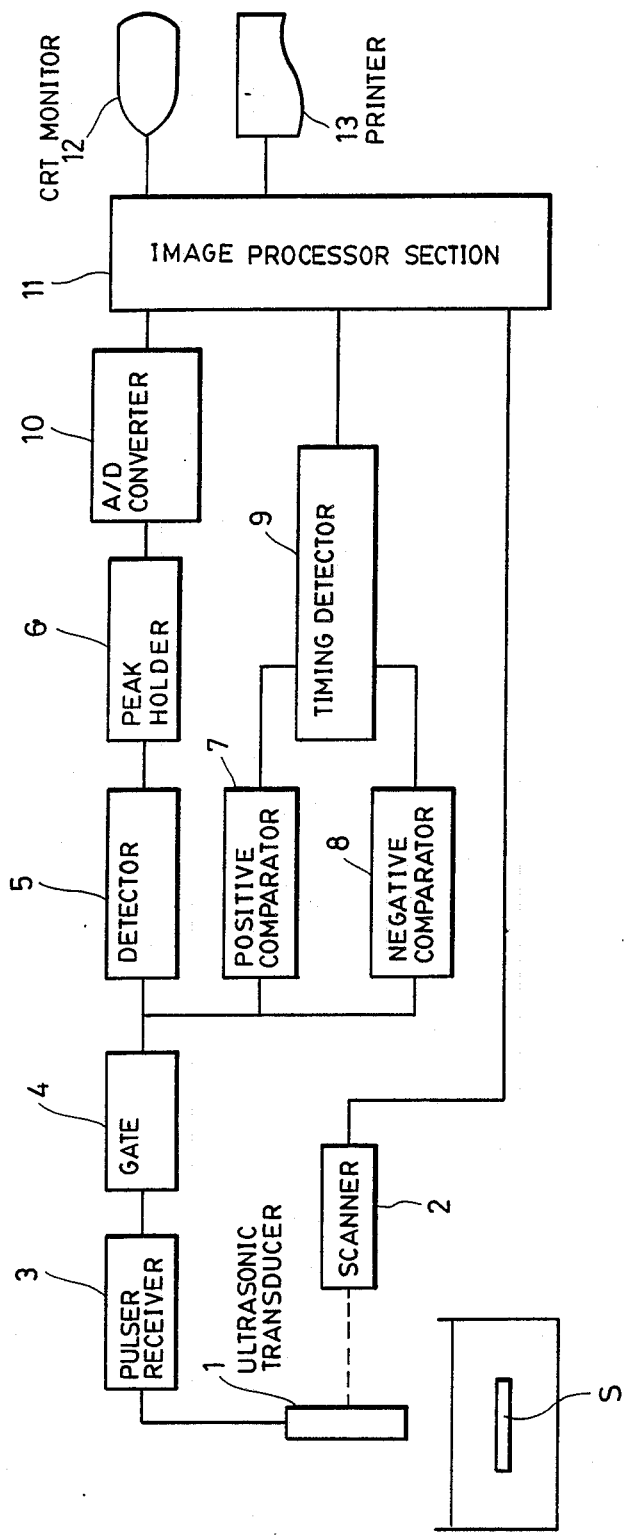
FIG. 1 is a block diagram showing a first embodiment of an ultrasonic measuring apparatus in accordance with this invention.

FIG. 1 is a block diagram showing the construction of an ultrasonic picture apparatus. An object S to be examined is disposed in a water tank so that it may be examined by the immersion method. An ultrasonic transducer 1 for transmitting and receiving an ultrasonic wave to and from the object S scans the object S by means of a scanner 2. Connected to the ultrasonic transducer 1 is a pulser receiver 3 adapted to apply a high-voltage pulse for transmitting the ultrasonic pulse and to amplify the reception signal. The output of a gate 4 is input to a detector 5 and then to a peak holder 6, whereby a signal at a level corresponding to that of the signal at the gate 4 is obtained. The output of the gate 4 is further input to a positive comparator 7 and a negative comparator 8, the outputs of the positive comparator 7 and the negative comparator 8 being commonly connected to a timing detector 9, whereby the signal rising direction is detected. The output of the peak holder 6 is quantized by an A/D converter 10, the outputs of the A/D converter 10 and the timing detector 9 being received by an image processor section 11, where the signal level is calculated and output, along with the positional information from the scanner 2, to a CRT monitor 12 and a printer 13.

Next, the procedures of the data-pickup processing will be described in order with reference to this embodiment.

Figure 4A:
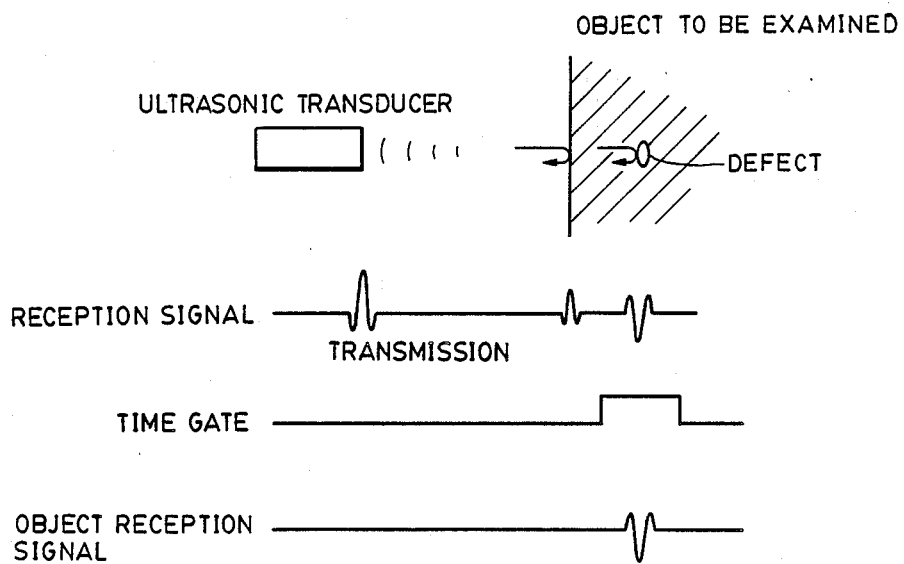
FIG. 4(a) illustrates the method of extracting a predetermined signal by passing a reception signal through a time gate.
Figure 4B:
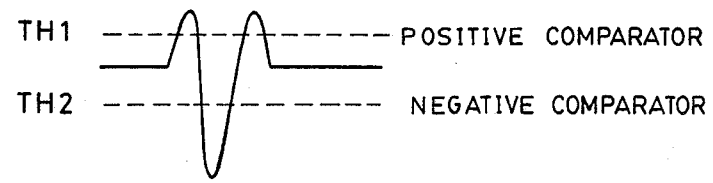
FIG. 4(b) illustrates how a predetermined reception signal is compared with a predetermined threshold using a comparator.

The ultrasonic pulse transmitted from the the transducer 1 by the high-voltage pulse from the pulser receiver 3 is reflected by the surface of the object S to be examined, the inner boundary surface thereof and the like, and is received by the ultrasonic transducer 1. The signal received is amplified by the pulser receiver 3 and is passed through a time gate of a suitable time constant at the gate 4, whereby the reception signal from the boundary surface concerned is extracted (see FIG. 4(a)). The signal extracted is detected by the detector 5. After its peak value (positive) is held by the peak holder 6, the signal is converted into a digital signal by the A/D converter 10. At the same time, the output of the gate 4 is compared with respective thresholds TH1 and TH2 by the positive and negative comparators 7 and 8 (see FIG. 4(b)). The outputs of the comparators are input to the timing detector 9, where their timing is compared with each other. If the output of the positive comparator is more advanced than that of the negative comparator 8, the logical value 1, if not, the logical value 0, is output to the image processor section 11. In the image processor section 11, the raising direction of the reception signal is distinguished on the basis of the signal from the timing detector 9. If it is in the same direction as the transmission pulse, the phase is judged to be the same (close-contact area) and the peak value (positive value) which is the output data of the A/D converter 10 is multiplied by −1. If it is in the reverse direction, the phase is judged to have been inverted and the above-mentioned peak value is multiplied by +1. The value obtained is stored as the measurement result. The measurement data obtained exhibits a negative value in close-contact areas. The larger the peeled area, the larger the value in the positive direction. If, conversely, the peak value is multiplied by +1 when the phase remains the same, and by −1 otherwise, the judgment will be made on the basis of the fact that the larger the value of the measurement data in the negative direction, the more defects such as peelings. Since the raising direction of the first transmission pulse emitted by the ultrasonic transducer can be determined beforehand through a combination of the pulser receiver 3 and the ultrasonic transducer 1 (negative in the case of FIG. 4(a)), the judgment as to whether or not the phase has been inverted can be made by comparing the output of the timing detector 9 with the raising direction of the transmission pulse thus determined previously.

By repeating the above-described operation while scanning the object S with the ultrasonic transducer 1 by means of the scanner 2, a reflection signal level distribution for various points on the surface of the object S can be obtained, and, by outputting the signal level to a CRT monitor and a printer 13 or the like signifying with color and brightness, an ultrasonic image can be obtained.

Other Embodiments

FIG. 2 shows a second embodiment of this invention.

The positive and negative peak values of the reflection signal, obtained in the same manner as in the first embodiment, are held by the positive and negative peak holders 14 and 15, the negative peak value being converted to a positive value by an inversion circuit 16.

The output of the positive peak holder 14 is compared with that of the inversion circuit 16. If the former is larger than the latter, the logic value of 0, and if not, the logic value of 1, is output to the image processor section 11.

The output of the positive peak holder 14 and that of the inversion circuit 16 are simultaneously input to a maximum value detector 18, the value of the larger of the two outputs being output to the A/D converter 10.

In the image processor section 11, the asymmetry of the reception signal is examined on the basis of the signal from a magnitude comparator 17. If the asymmetry is the same as that of the transmission pulse, the phase is judged to be the same, and the output data of the A/D converter 10 is multiplied by the value −1. Otherwise, the phase is judged to have been inverted, and the output data of the A/D converter 20 is multiplied by +1. The value obtained through the multiplication is stored as the measurement data.

FIG. 3 shows a third embodiment of this invention.

The reflection signal obtained in the same manner as in the above embodiments is successively digitized by a sample holder 19 and an A/D converter 20, and is stored in a waveform memory 21. In a data processor section 22, the phase and the peak value of the reception signal are obtained through calculation from the data of the waveform memory, and are output to the image processor section 11. The judgment as to whether or not a phase inversion has occurred may be made in the same manner as in the first embodiment. Namely, the phase of the reception signal may be ascertained from the signal raising direction which can be inferred from the timing of the intersections between the positive and negative thresholds and the signal data. Alternatively, the phase of the reception signal may be ascertained, as in the second embodiment, by obtaining maximum and minimum values and comparing their absolute values with each other.

If the capacity of the waveform memory 21 is large enough to store the waveform data on all the measurement points, the signal level can be calculated with parameters such as the phase detection method and the thresholds being changed after the data has been picked up.

Although the present invention has been described in connection with several preferred embodiments, it will be apparent to those of ordinary skill in the art that many changes and modifications may be made therein without departing from the scope of the present invention, which is to be determined by reference to the appended claims.

What is claimed is:

1. An ultrasonic measuring apparatus for measuring a predetermined boundary surface inside an object, comprising:

pulse generating means for transmitting an ultrasonic pulse to the object;

moving means for moving said pulse generating means in two dimensions relative to said object;

reception means for receiving a reception signal generated when said ultrasonic pulse is reflected by the object;

means for taking a reflected signal out from the boundary surface, passing the reflected signal through a time gate according to the depth of the boundary surface to be examined inside the object;

level detection means for detecting a level of a reflected signal from the boundary surface, and producing an output;

phase detection means, different from said level detection means, for detecting a phase of a reflected signal from the boundary surface, and producing an output;

means for providing the output from said level detection means with either a positive or a negative sign in accordance with the output from said phase detection means and for outputting the output from said level detection means provided with positive or negative signs as measurement data;

memory means for storing each measurement data obtained at each measurement position on the boundary surface; and means for forming and outputting an ultrasonic image of the boundary surface, in two dimensions, in accordance with the data of each measurement position on the boundary surface stored in said memory means.

2. An apparatus as claimed in claim 1, wherein said phase detection means conducts phase detection by comparing the rising direction of the transmission pulse signal with that of said reception signal.

3. An apparatus as claimed in claim 2, wherein said detection means includes a positive comparator and a negative comparator, and wherein the rising direction of said reception signal is detected by comparing the timing of respective output signals of said positive and said negative comparator with each other.

4. An apparatus as claimed in claim 3, wherein said phase detection means performs analog-to-digital conversion of the reception signal so as to detect the phase thereof through calculation.

5. An apparatus as claimed in claim 1, wherein said pulse generating means employs an asymmetrical signal as the transmission pulse, and wherein said phase detection means includes a positive peak holder and a negative peak holder and performs phase detection by comparing the magnitudes of output signals from said positive and said negative peak holder with each other.

6. An apparatus as claimed in claim 5, wherein said phase detection means performs analog-to-digital conversion of the reception signal so as to detect the phase thereof through calculation.

7. An apparatus as claimed in claim 1, wherein the object to be examined is disposed in water and the ultrasonic pulse is transmitted through the water.

* * * * *